US00PP29580P3

(12) United States Plant Patent
Higaki

(10) Patent No.: US PP29,580 P3
(45) Date of Patent: Aug. 7, 2018

(54) ***HYDRANGEA* PLANT NAMED 'BCHY-11.028'**

(50) Latin Name: ***Hydrangea macrophylla* (Thunb.)**
Varietal Denomination: BCHY-11.028

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 14/999,150

(22) Filed: Apr. 4, 2016

(65) Prior Publication Data

US 2017/0290224 P1 Oct. 5, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Keith O Robinson
(74) *Attorney, Agent, or Firm* — James R. Cypher; Charles R. Cypher

(57) ABSTRACT

A new and distinct cultivar of *Hydrangea macrophylla* (Thunb.) named 'BCHY-11.028' originated as a controlled cross between varieties. The variety 'BCHY-11.028' has attractive inflorescences with relatively large sepalous florets, attractive, uniform sepal pigmentation and good commercial characteristics. Many non-sepalous florets in the center of the inflorescence make the new variety look similar to a lace-cap variety.

3 Drawing Sheets

Botanical classification: *Hydrangea macrophylla* (Thunb.) 'BCHY-11.028'.

Variety denomination: 'BCHY-11.028'.

BACKGROUND OF THE INVENTION

This invention relates to a new and distinct cultivar of the Saxifragaceae family. The botanical name of the plant is *Hydrangea macrophylla* (Thunb.) 'BCHY-11.028'.

The new cultivar originated as a seedling from a controlled cross between a variety known to the inventor as 'BCHY-06.014' (unpatented) which was the seed parent and the patented variety known as 'BC8.3' U.S. Plant Pat. No. 25,507 which was the pollen parent. 'BCHY-06.014' was the subject of U.S. patent application Ser. No. 13/999,982 which was abandoned. 'BCHY-06.014' originated as a seedling from a controlled cross between the unpatented variety known as 'LK49' which was the seed parent and a commercial variety known as 'Venedig' to the inventor which may be the subject of U.S. Plant Pat. No. 10,928 and registered as 'Venice Raven'. 'Venedig' was the pollen parent of that cross. 'LK49' is relatively compact plant with wiry stems, relatively small leaves, relatively small sepalous florets, and inflorescences that are resistant to being damaged by conditions in commercial coolers. 'BCHY-06.014' has strong stems, attractive inflorescences, and develops very deep pigmentation when treated with aluminum at commercial levels, and even if treated with only a relatively small amount of aluminum it develops a uniform and attractive pigmentation. 'BC8.3' is the subject of U.S. Plant Pat. No. 25,507 that issued on May 5, 2015. 'BC8.3' originated as a seedling from a controlled cross between the commercial variety known as 'Nizza' to the inventor, and a commercial variety known as 'Messalina' to the inventor. The inventor is not aware if 'Nizza' and 'Messalina' are parented. 'BC8.3' has compact, attractive inflorescences with relatively large sepalous florets that ring and almost hide all of the non-sepalous florets in the center of the panicle, attractive sepal pigmentation, grows well under commercial conditions, and stems that branch easily and are relatively strong.

The variety 'BCHY-11.028' has relatively large sepalous florets, non-uniform sepal pigmentation at maturity and good commercial characteristics. 'BCHY-11.028' has compact, attractive inflorescences with relatively large sepalous florets that surround the non-sepalous florets in the center of the panicle. The color of the sepals changes as the plant ages. Below is a table comparing the new variety to similar varieties, including the variety 'BCHY-11.068' which is the subject of copending U.S. patent application Ser. No. 14/999,149 and resulted from the same series of crosses. The new variety 'BCHY-11.028' differs from copending variety 'BCHY-11.068' in that non-sepalous florets of the inflorescence of 'BCHY-11.068' are hidden by the sepalous florets while the non-sepalous florets of 'BCHY-11.028' are ringed and not hidden by the sepalous florets, the minority of buds of 'BCHY-11.028' develop into sepalous florets, the inflorescence of the new variety 'BCHY-11.028' is flat while the inflorescence of 'BCHY-11.068' is globose, and the sepals and florets of 'BCHY11.028' are larger than those of 'BCHY-11.068'.

TABLE 1

| | New Variety 'BCHY-11.028' | U.S. Plant Pat. No. 23,757 'BC6.1' | U.S. Plant Pat. No. 25,507 'BC8.3' |
|---|---|---|---|
| Leaf size | 8.5 cm wide × 14 cm long | 12 cm wide × 15 cm long | 10 cm × 16 cm |

TABLE 1-continued

| | | | |
|---|---|---|---|
| Plant height | 14" in 6" pot. | 15" in 6" pot. | 15" in 6" pot |
| Stem strength | Strong | Stems are strong but benefit from being staked | Stems are relatively strong. |
| Sepal Pigmentation | Both sides of sepals are R.H.S. 72 C (red - purple group). | Upper side of sepals is R.H.S. 86 A (violet group); Under side of sepals is R.H.S. 88 D (violet group) | Upper side of sepals is R.H.S. 73A (red - purple group) in center, and margins of sepals are R.H.S. 56 A (red group). |
| Sepalous Floret Size - Diameter | 75 mm | 70 mm | 50 mm to 60 mm |

| | Commerical variety 'Venedig' which may be U.S. Plant Pat. No. 10,928 'Venice Raven' | U.S. Plant patent application Ser. No. 14/999,149 'BCHY-11.068 | U.S. Plant patent application Ser. No. (abandoned) 13/999,982 'BCHY-06.014' |
|---|---|---|---|
| Leaf size | 11 cm wide × 15.5 cm long - source U.S. Plant Pat. No. 10,928 | 10.5 cm wide × 14 cm long | 9 cm wide × 13.5 cm long |
| Plant height | 12" in 6" pot - observed controls grown alongside 'BC6.1'. | 15" in 6" pot. | 18" in 6" pot. |
| Stem strength | Strong - observed controls grown alongside 'BC6.1'. | Strong | Strong |
| Sepal Pigmentation | Upper side of sepals is R.H.S. 84 A (violet group). Under side of sepals is R.H.S. 85 A (violet group) observed controls grown alongside 'BC6.1'. | Upper sides of sepals are R.H.S. 94 A (violet - blue group). Under sides of sepals are R.H.S. 96 D (violet - blue group). | Treated With Aluminum - Mature inflorescences - Both sides of sepals are R.H.S. 95 B (violet - blue group). |
| Sepalous Floret Size - Diameter | 70 mm - observed controls grown alongside 'BC6.1'. | 55 mm | 60 mm |

The new cultivar 'BCHY-11.028' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BCHY-11.028' remains firmly fixed.

DESCRIPTION OF THE DRAWINGS

The accompanying drawings consist of color photographs that show the typical plant form at 1 year when grown in a commercial nursery and forced to bloom, including the inflorescence, foliage, and sepals.

DESCRIPTION OF THE NEW PLANT

Figure 1:
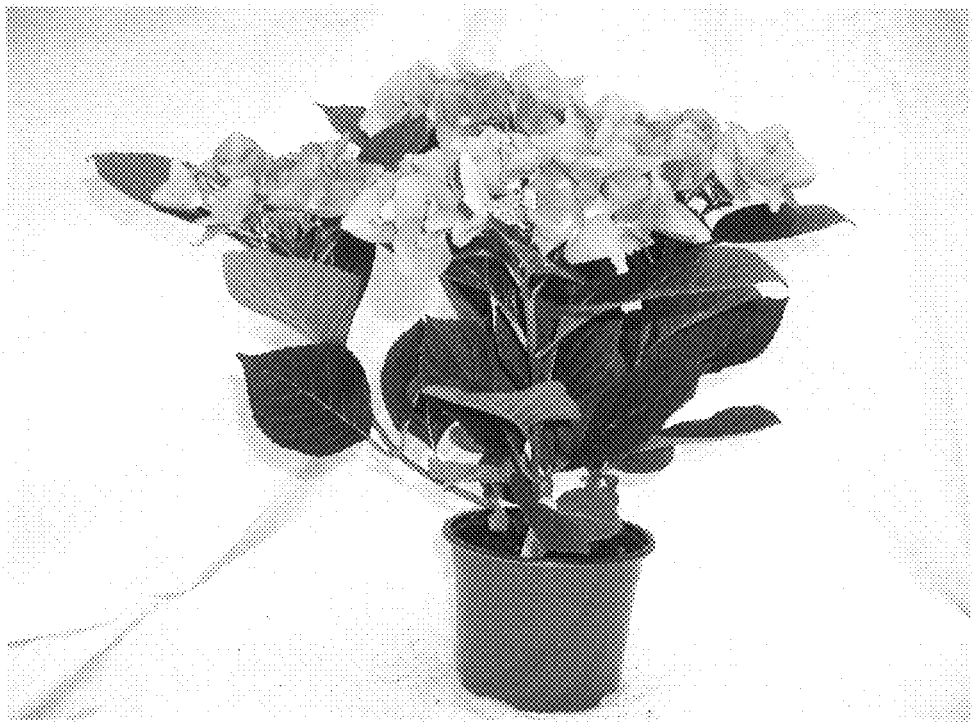
FIG. 1 is a view of the new variety showing its form.
Figure 2:
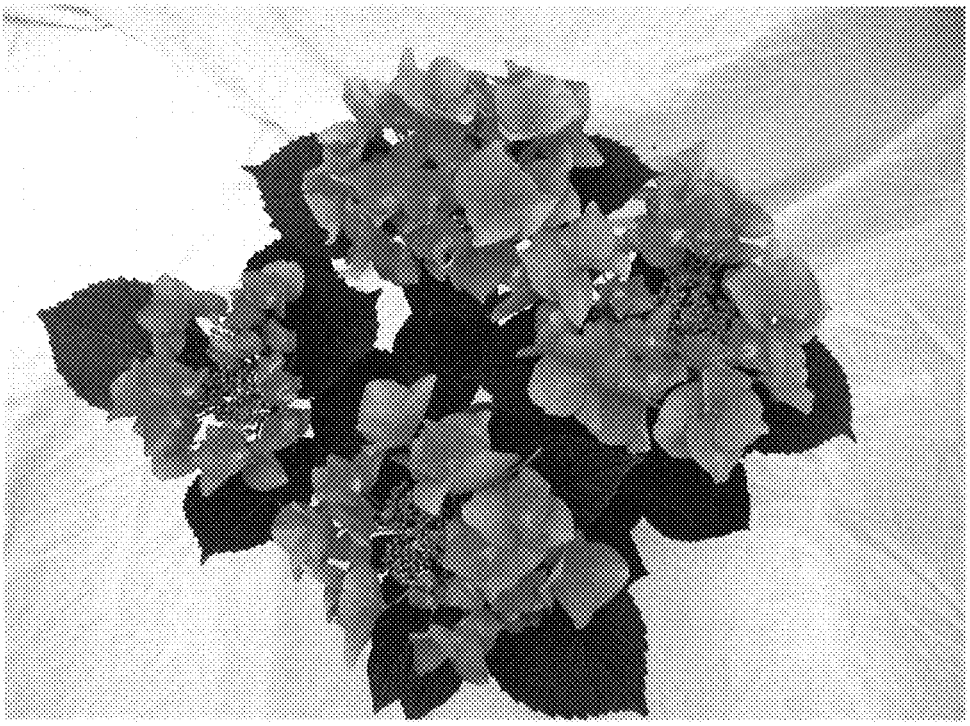
FIG. 2 is a top view of multiple inflorescence of the new variety.
Figure 3:
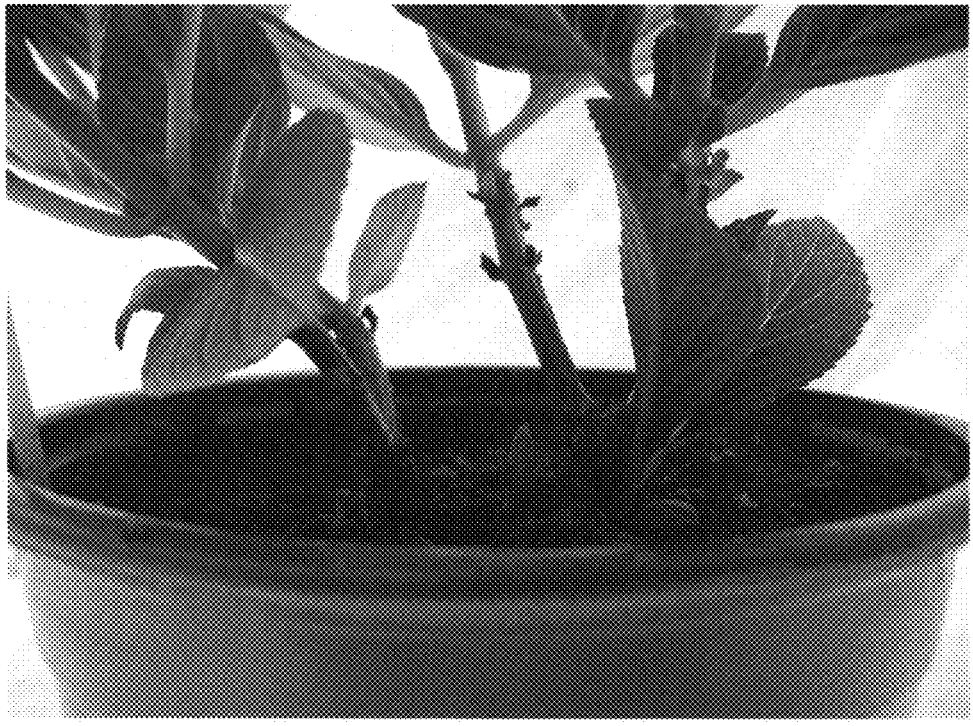
FIG. 3 is a close-up view of the base of the plant of the new variety.
Figure 4:
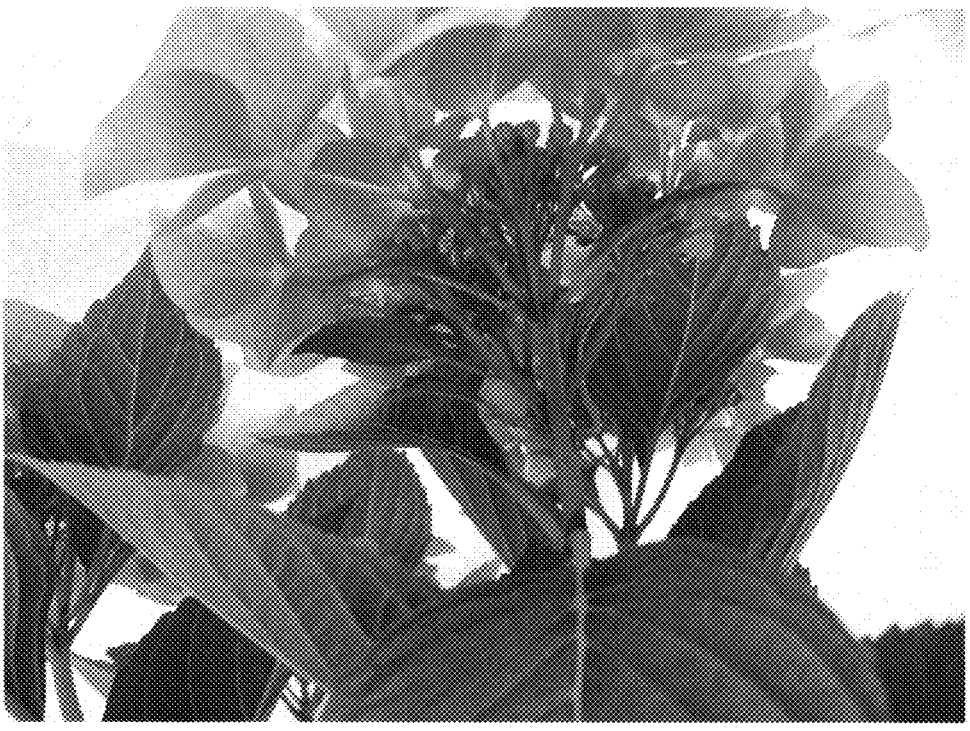
FIG. 4 is a close-up view of the top of the inflorescence of the new variety.
Figure 5:
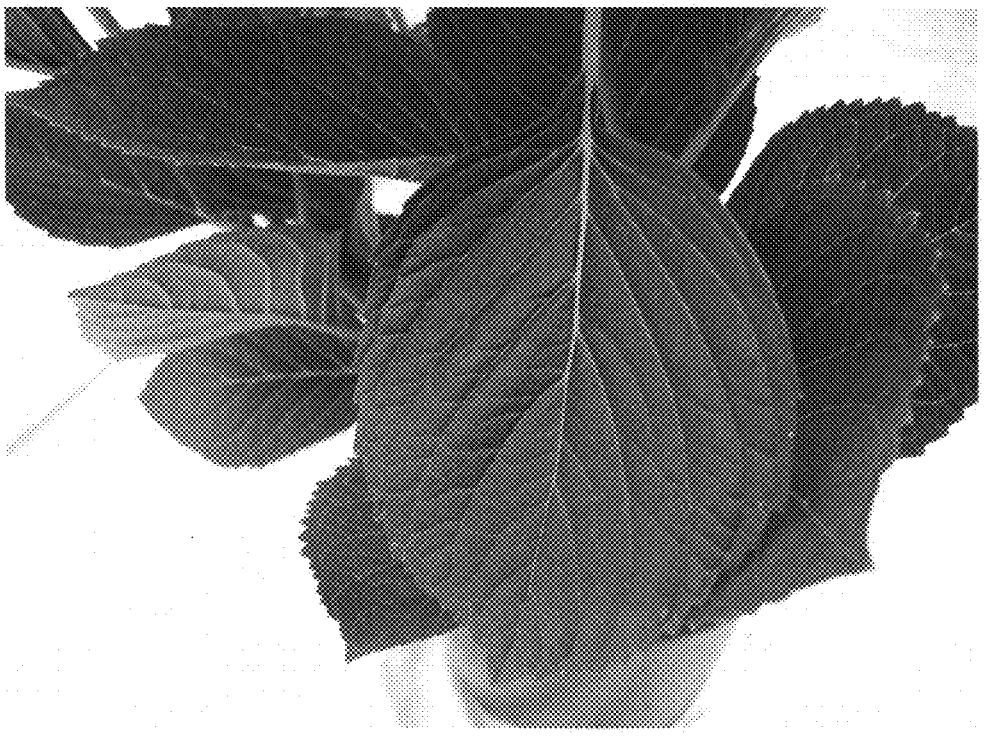
FIG. 5 is a close-up view of a number of inflorescences of the new variety.
Figure 6:
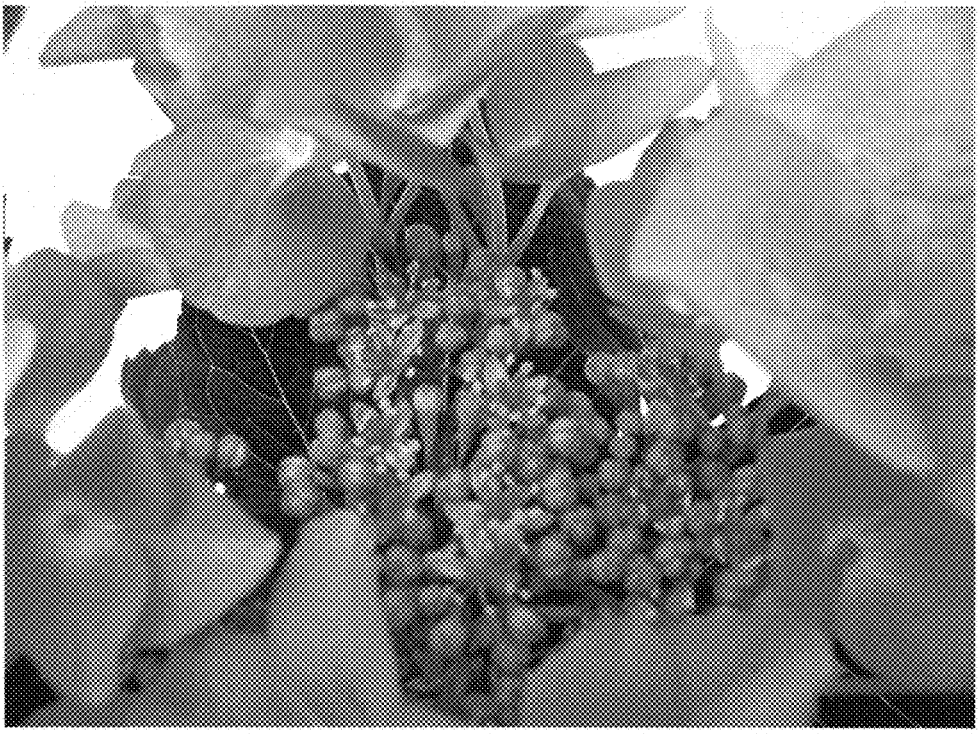
FIG. 6 is a close-up view of several new florets of the new variety.

The plant described is approximately a year old. The plant started out as cuttings, used from the stem of a grown plant. The soil for the plant was periodically treated with aluminum to produce blue pigmentation. The plant was pinched early to promote lateral branches.

'BCHY-11.028' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden. The plant:

*Origin.*—Controlled cross. The new cultivar originated as a seedling from a controlled cross between the unpatented variety known as 'BCHY-06.014' which was the seed parent, and the patented variety 'BC8.3' — U.S. Plant Pat. No. 25,507 — which was the pollen parent.

*Form.*—Upright, non-climbing, compact shrub. The mature plant, including a mature inflorescence, that is ready for sale is approximately 14" high and has a diameter of 18" when grown in a 6" pot with appropriate soil amendments.

*Growth.*—Upright, vigorous growth habit. Inflorescence is large. The plant branches easily with shoots forming at the base of the plant. Lateral branches are similar in appearance and form to the main stems.

*Stems.*—Stems are 11" long. Fasciation is absent. Lenticels are present. Lenticels are R.H.S. 86 A (violet group) and are 1 to 2 mm long. The surface of young stems is glabrous. Stems become woody as they age. The color of typical young stems and young lateral branches is R.H.S. 145 A (yellow-green group). The older portions of the stems are R.H.S. 199 A (grey-brown group). Younger portions of the stems are 7 mm in diameter. Older portions of the stems are 7 mm in diameter.

*Foliage.*—Abundant. Leaves are opposite on stem and lateral branches. Shape of leaf. — Elliptic with acute base and acute apex. Leaf blade margins are serrate and not lobed. Texture. — Glabrous; veins dominate on the underside of the leaf and are sunken on the upper leaf surface. Color. — Mature leaves have an upper side that is R.H.S. 136 A (green group), and an under side that is R.H.S. 138 B (green group). Leaves are moderately glossy. Variegation is absent. Leaves are pinnately veined. The midvein and veins branching off the midvein are large and prominent on the underside of the leaves. Veins are R.H.S. 145 C (yellow-green group). Leaves are as wide as 8.5 cm and 14 cm long. Petioles are smooth and approximately 2.0 cm long and 4 mm wide. Petioles are R.H.S. 145 C (yellow-green group).

Buds:

*Form.*—Globose with 4 to 5 connate, elliptic, smooth petals. Most buds, whether they will mature into sepalous or non-sepalous florets, have 4 petals. Buds in the center of the inflorescence are non-sepalous. The minority of buds will develop into sepalous florets. They are approximately 2 mm by 2 mm when very young. Buds can be 5 mm in diameter and still unopened. Color of mature buds is R.H.S. 77 B (purple group).

*Aspect.*—Smooth.

*Arrangement.*—Borne on branched panicles.

Inflorescence:

*Form.*—Paniculate. Terminal. As many as 150 individual florets (both sepalous and non-sepalous) per inflorescence. Both sepalous florets and non-sepalous florets borne on the same panicle. Non-sepalous florets are conspicuous. Flowers do not produce a fragrance. The peduncle for the inflorescence is strong and upright. Many non-sepalous florets developing early on cymes. Florets, both sepalous and non-sepalous, have anthers and style. Inflorescences are long-lasting.

*Size of inflorescence.*—Compact and flat. Individual inflorescence size is dependent on the number of florets. A typical inflorescence can grow as large as 8" in diameter, and 3" high.

*Shape.*—Clusters of numerous small florets; sepalous florets overlap one another. Sepals are persistent.

*Appearance.*—Showy.

Florets:

*General.*—The non-sepalous florets at the center of the inflorescence open first. Sepalous and non-sepalous florets are perfect and complete. Corolla: Generally, for both sepalous and non-sepalous florets there are 4 petals which fall off as the floret matures. Petals are typically 4 mm long and 3 mm wide. Petals are R.H.S. 77 B (purple group). Lenticels are present, but relatively few, on pedicels of both sepalous and non-sepalous florets, lenticels are no more than 1 mm to 4 mm long and very narrow. Lenticels are R.H.S. 59 B (red purple group). Pedicel length for non-sepalous florets averages 4 mm. Pedicel length of sepalous florets is approximately 25 mm in length for plants of this age. Pedicels of both sepalous and non-sepalous florets continue to elongate as the inflorescence ages. Pedicels range from 73 A (red purple group) to R.H.S. 145 A (yellow-green group) near floret when mature.

*Stamens.*—8 to 10 stamens. Anther is regular and basally attached. Filament is approximately 4 mm long. Filament is R.H.S. 77 B (purple group). Anther is 1 mm long and is regular and basally attached. Pollen is scarce.

*Stigma.*—Two to three style each, although most florets have two style. Each style has one stigma. Style is 1 mm long. Style is R.H.S. 77 B (purple group). Stigma is R.H.S. 77 a (purple group).

*Ovary.*—Ovary is partially inferior.

*Sepalous florets.*—General. — Veins dominate on the underside of the sepals. Number of sepals. — 4 to 5 sepals per floret, usually 4. Aspect of sepals. — Smooth and glaucescent. Shape of sepals. — Reniform with acuminate apex. Edges are entire, but with some crenation. Size of sepals. — As the florets mature, the sepals enlarge and overlap each other more and more, until, often, there is no space between the sepals when the petals of the florets open. Sepals at maturity are typically 40 mm long and 40 mm wide. Sepalous florets are typically 75 mm in diameter. The upper sides of the sepals are R.H.S. 72 C (red-purple group) and the undersides are the same. Pigmentation develops at the tips of the sepals and travels inward towards base of the sepals. Pigmentation lightens as the sepals reach maturity. Pigmentation of older florets is 73 A (red-purple group).

*Fruit.*—None.

*Disease and pest resistance.*—Unknown. Plants prefer milder temperatures. Plants bloom in the spring but can be forced to bloom by placing in a cold environment.

I claim:

1. A new and distinct *Hydrangea macrophylla* plant named 'BCHY-11.028' substantially as herein illustrated and described.

* * * * *